United States Patent [19]

Pierre et al.

[11] Patent Number: 4,806,408
[45] Date of Patent: Feb. 21, 1989

[54] ABSORBENT STRUCTURE FOR DISPOSABLE ARTICLES

[75] Inventors: Michel Pierre, Mulhouse; Rémy Ruppel, Horbourg; Jean Brellmann, Colmar, all of France

[73] Assignee: Beghin-Say SA, Thumeries, France

[21] Appl. No.: 932,478

[22] PCT Filed: Feb. 6, 1986

[86] PCT No.: PCT/FR86/00033
§ 371 Date: Nov. 3, 1986
§ 102(e) Date: Nov. 3, 1986

[87] PCT Pub. No.: WO86/05089
PCT Pub. Date: Sep. 12, 1986

[30] Foreign Application Priority Data

Mar. 1, 1985 [FR] France .................. 85 03016

[51] Int. Cl.⁴ .................. A61F 3/16; A61F 3/18
[52] U.S. Cl. .................. 428/76; 428/138; 428/323; 428/534
[58] Field of Search .................. 428/534, 76, 323, 138

[56] References Cited

U.S. PATENT DOCUMENTS

| | | | |
|---|---|---|---|
| 1,755,113 | 4/1930 | Grom | 132/73 |
| 3,070,095 | 12/1962 | Torr | 428/323 |
| 3,661,154 | 5/1972 | Torr | 604/375 X |
| 3,903,889 | 9/1975 | Torr | 428/153 X |
| 4,144,886 | 3/1979 | Holst et al. | 428/534 X |
| 4,485,133 | 11/1984 | Ohtsuka et al. | 428/35 |
| 4,487,791 | 12/1984 | Komatsu et al. | 428/35 |
| 4,690,853 | 9/1987 | Hammond | 428/172 X |

FOREIGN PATENT DOCUMENTS

| | | | |
|---|---|---|---|
| 2004201 | 3/1979 | United Kingdom | 428/534 |
| 2014046 | 8/1979 | United Kingdom | 428/137 |

Primary Examiner—Henry F. Epstein
Attorney, Agent, or Firm—A. W. Breiner

[57] ABSTRACT

An absorbent structure for disposable articles, comprising between a permeable sheet (1) and an impermeable sheet (7), a pad comprising successively at least one fibre layer (2, 12, 22, 32), an internal reinforcement sheet permeable to liquids and an absorbent layer provided with improved retention additive particles is characterized in that the internal reinforcement (3, 13, 23, 33) is a non-woven material maintained by gluing (4, 14, 24, 34) to said absorbent layer (5-6, 15-16, 25, 35-36).

8 Claims, 2 Drawing Sheets

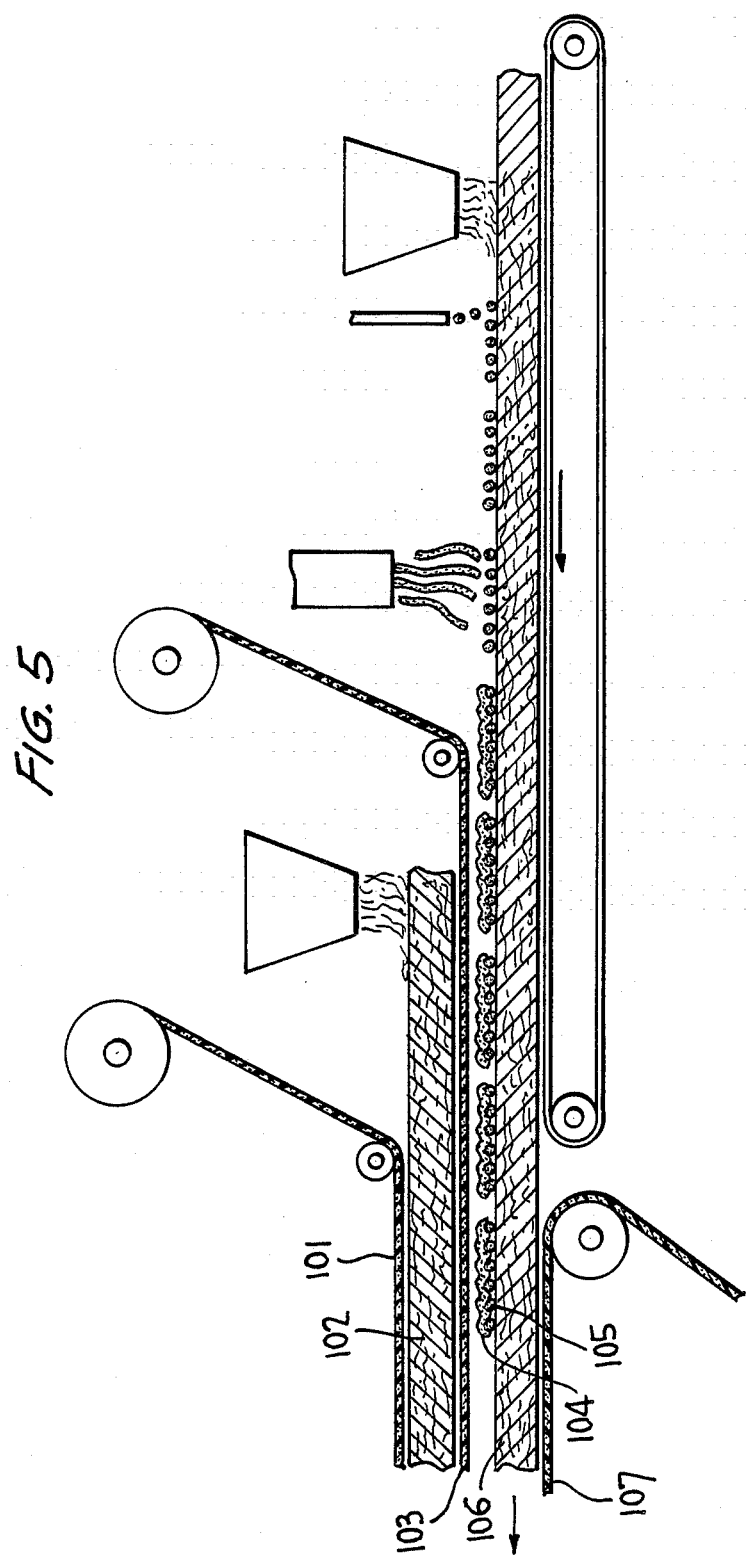

ABSORBENT STRUCTURE FOR DISPOSABLE ARTICLES

The invention covers an absorbent structure for disposable articles such as a baby's nappy, a sanitary pad or any other article intended to absorb and retain body secretions and be discarded after use.

This type of article generally comprises a mass absorbing the liquids placed between a permeable web on the body side and an impermeable sheet of polyethylene on the external side.

The absorbent mass usually consists of one or several cellulose fibre layers of cellulose fibres obtained by dry defibration of paper pulp sheets or rolls.

In order to improve the absorbent power of the pad and limit its volume improved retention additives known also as superabsorbents are incorporated in it. These additives, which are in the form of fibres, film or more generally granule particles or pellets are compounds which swell in the presence of the liquid to be absorbed, but they are not solubilized. The liquid is then absorbed quasi-irreversibly, at least under the usual utilization conditions, and form with the compound a gel whose volume can be several tens of times greater than that of the dry additive.

According to most of the known methods the superabsorbent particles are fixed on the surface of the pad or incorporated in its mass. The terms "fixed" and "incorporated" mean that there is a rigid bond between a particle and the pad obtained by the presence of an additive providing adhesion.

For example, from FR Pat. No. 2,402,474 it is known that there is method for the manufacture of an absorbent structure in which an improved retention additive is combined with a substrate, and then fixed by the deposition of a binder by spraying or transfer. The substrate can be a synthetic film or a fibrous material constituting the external face. According to one of the forms of embodiment of the patent the additive layer is covered with a second fibrous pad before the permeable web on the body side is placed in position.

According to FR Pat. No. 2,446,357, the additive is contained, without being fixed, between two fibrous layers bonded to one another along lines of the points of cohesion. These layers thereby delimit a number of receptacles in which the gel can develop freely.

According to another known method a nappy for babies is made by successively placing on a sheet of soft tissue, a pad of foamed cellulose, then a layer of superabsorbent in a narrow, central strip and a sheet permeable to liquids of the size of the superabsorbent strip. The lateral edges of the sheet of soft tissue and the pad not covered with superabsorbent are then folded over one another onto the permeable sheet. A layer with a cross-section in the form of a snail is thereby obtained, with a triple thickness of cellulose foam enclosing the superabsorbent.

These various methods allow the products with a good liquid absorption capacity to be produced.

However it has been found in a certain percentage of articles comprising one of the structures described above that the gel becomes visible after normal usage. This occurs when the additive is incorporated in the mass in depth in a manner such as to leave on the body side immediately under the permeable sheet a cellulose foam layer free from or poor in additive allowing the diffusion of the liquid towards the layers next to the impermeable external sheet.

The fact that the gel becomes visible may be due to the loss in cohesion of this layer facilitated by the baby's movements. This may also be due to the migration of the gel through this layer. When a permeable sheet is introduced between the additive and the upper fluff layer an improvement is found; but it is not significant, migration also takes place through the meshes or the perforations of the sheet, or else the gel circumvents it. Such migration is not desirable as it promotes pilling of the layer to the detriment of the comfort of the user. In addition poor distribution results in a barrier effect by the gel formed in certain places thereby increasing the risks of leaks. Under extreme utilisation conditions the gel can pass through the permeable web on the body side and become deposited on the skin of the body. The viscous consistency of this gel, although harmless, is certainly not very attractive and increases the feeling of discomfort.

According to U.S. Pat. No. 3,903,889 one or several sheets of soft tissue are placed between the absorbent mass charged with superabsorbent particles and the upper permeable web. A layer of glue bonds the first sheet to the absorbent mass. In use, such a structure does not give satisfaction as the soft tissue sheets do not resist moisture and do not sufficiently oppose the pressure of the underlying gel, in addition the combination of several sheets with the object of improving moisture resistance has the disadvantage of being detrimental to the rapid diffusion of liquids and increases the risks of leaks.

The object of the invention is therefore to overcome these disadvantages; it provides an absorbent structure with improved strength properties, which greatly reduces the risk of the gel rising under the surface of the permeable sheet on the body side.

In accordance with the invention an absorbent structure for disposable articles comprising, between a permeable sheet on the body side and an opposite impermeable sheet, a pad comprising at least one cellulose fibre layer, an internal reinforcement sheet permeable to liquids and an absorbent layer comprising improved retention additive particles is characterized in that the reinforcement sheet is a non-woven material maintained in position by gluing to said absorbent layer.

A non-woven is a manufactured product of extended area compared with its width consisting of individual fibres orientated in one direction or randomly bonded by a physical or chemical process, to the exclusion of paper and products obtained by weaving, knitting, felting, etc. The fibres can be of natural or chemical origin and of finite or non finite length, they can even be formed in situ. In its application to the invention an non-woven material is distinguished from paper by the fact that it does not tear in the moist state under pressure of the gel which therefore remains masked.

Thus the transversal moist strength of a test piece 200 mm long and 50 mm wide is less than 150 cN for a 50 $g/m^2$ grammage multi-ply paper whereas for a 20 $g/m^2$ grammage non-woven material it must be above 200 cN.

According to a preferred embodiment the gluing is effected by the deposition of hot melt glue, a method known in English as "spray hotmelt".

Without adversely affecting the absorptive capacity of the structure and while allowing the additive particles to develop without hindrance, gluing provides great structural stability; the tests performed have shown a surprising improvement as regards the proportion of gel visible after use. This proportion is defined as the ratio of the number of nappies in which the gel is visible after use to the number of nappies examined.

BRIEF DESCRIPTION OF THE DRAWINGS

Other characteristics and advantages are developed in the detailed specification that follows, referring to four non-limitative modes of embodiment of the invention and in which:

FIG. 3 shows a cross-section of a third mode of embodiment FIG. 5 shows a flowsheet of a method for the manufacture of the structure according to FIG. 1.

FIG. 1 shows schematically the cross-section of a disposable article which later will be considered as being a nappy for babies, for the sake of clarity; the components are placed in accordance with a first mode of embodiment of the invention.

Figure 1:
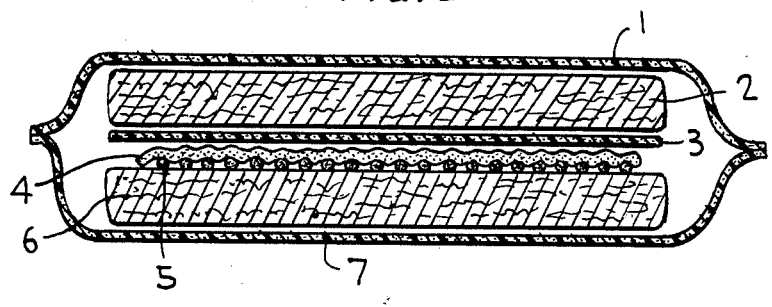
FIG. 1 shows the cross-secton of a first form of embodiment of the absorbent structure according to the invention

This nappy is covered on its upper face, the face that comes into contact with the skin of the baby, by a sheet permeable to body liquids. This sheet can be an impermeable sheet perforated by a multiplicity of holes or else a non-woven material such as that sold under the trademark Holnest which is web of heat-bonded polypropylene fibres. Other types of permeable sheets may also be used.

The absorbent pad, as such, consists of a first cellulose fibre layer 2, a cellulose foam for example comprising or not comprising synthetic fibres.

Under layer 2 is placed an internal reinforcement sheet 3, permeable to liquids, of the same width as layer 2.

This reinforcement sheet can be of the same nature as external sheet 1 or of different nature. But it must be sufficiently strong for cohesion to be maintained after wetting; this therefore excludes soft tissue sheets. This sheet shall preferentially be of a lower grammage than the exterior permeable sheet.

It can, for example, be a grid according to the information contained in FR Pat. No. 2,195,555 and known under the trademark of Scrinyl, a polypropylene grid reinforced with polyamide filaments, or else a web of bonded thermoplastic fibres, like Holnest. The non-woven material 3 is maintained on a second fibre layer 6, of the same nature as the first, by means of a binder 4. The binder can be of the type commonly used in similar applications, for example a polyvinyl alcohol which is deposited by spraying a dilute dispersion of the binder. But this type of binder, when diluted, has the disadvantage of moistening the substrate during manufacure which adds to costs.

For these reasons a binder of the "Spray Hotmelt" type is preferred. This is a method for hot spraying filments with hot melt glue, for example that sold under the trademark Belix 74101 by Bericol.

The purpose of the binder is also to maintain the superabsorbent particles 5 placed in one layer on the fibre pad 6.

These additives can be ionic like Enka'Akucel which is a cellulose derivative of the CMC cross-linked type, Sanyo's Sanwet, Henkel's SGP or Grain Processing Corp.'s A-100, which are starch derivatives, Stock-Hausen's Favor, Nippon Shokubai's Aqualic, Seitsu's Aquaqeep, which are synthetic derivatives. These additives can also be non-ionic of the hydroxycellulose or cross-linked polyethylene type and are then not very sensitive to the salinity of liquids.

This absorbent structure is covered on its external face opposite face 1 by a polyethylene sheet 7 impermeable to liquids. Sheets 1 and 7 are bonded by their edges so as to enclose the absorbent pad.

Figure 2:
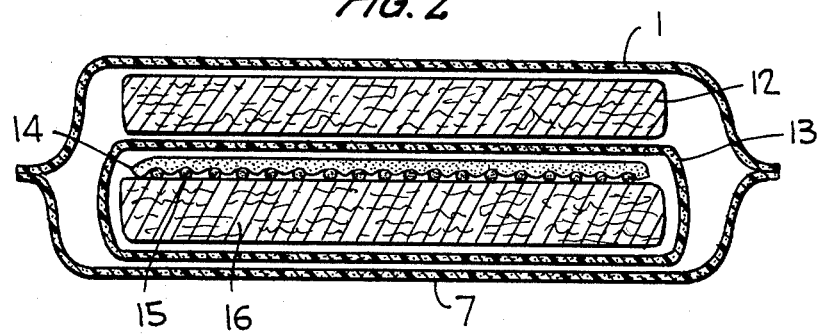

FIG. 2 shows a second mode of embodiment of the invention.

In this variant reinforcement sheet 13 extends around the second layer 16 in a manner such as to form an envelope of layer 16 and additive 15. This ensures still better maintenance of the gel in position. Glue 14 maintains both reinforcement sheet 13 and additive 15 on layer 16.

Figure 3:
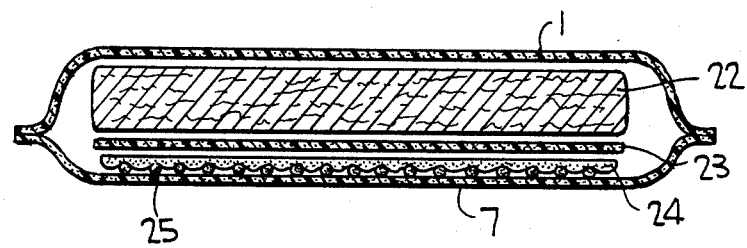
FIG. 3 shows the cross-section of a second mode of embodiment
Figure 4:
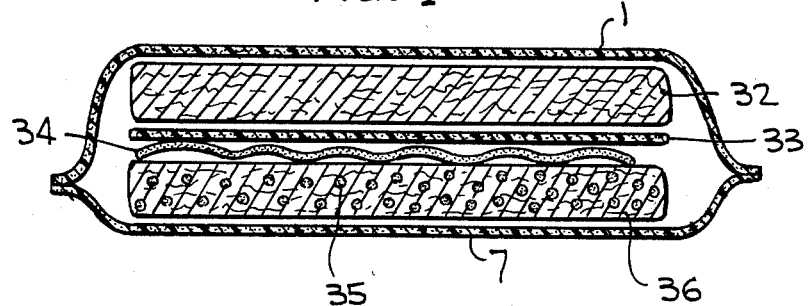
FIG. 4 shows a cross-section of a fourth mode of embodiment

FIG. 3 shows a third mode of embodiment in which the lower fibre layer has been omitted. The second absorbent layer therefore consists solely of improved retention additive 25, glue 24 maintain reinforcement sheet 23 against impermeable sheet 7. FIG. 4 shows a fourth mode of embodiment in which the additive particles 35 are incorporated in the mass of second layer 36, the non-woven material 36 being fixed by binder 34 to this layer 36.

FIG. 5 shows a flowsheet of the method of the manufacture of the structure according to the first mode of embodiment.

The cellulose foam is deposited as a layer 106 of uniform thickness on a conveyor belt, a nozzle deposits at regular intervals a layer of a defined quantity of superabsorbent particles 105; it passes under a hot spraygun of filaments of hot melt glue 104 (this spraygun comprises a nozzle by means of which the molten glue is injected into a current of hot air; the latter bursts the jet of glue into filaments). Then a sheet of non-woven material 103 is placed on the glue. On this sheet is placed a layer 102 of cellulose foam of uniform thickness. This assembly is the transferred onto polyethylene sheet 107 and an upper permeable sheet 101 completes the structure which is the calendered, sealed and cut out to form the desired article.

Comparative tests have been carried out in a nursery to test complete nappies manufactured according to the first mode of embodiment of the invention.

These were nappies comprising two superimposed cellulose foam layers each of 450 g/m$^2$ grammage, the additive being Sanwet at a rate of 1.5 to 2 g per nappy. The upper permeable sheet was Holnest of 19 g/m$^2$ grammage, the impermeable sheet of polyethylene. Six batches each of two hundred nappies were made up; the batches were respectively:

(1) without internal sheet (2) with an internal reinforcement grid made of Scrinyl (9 g/m$^2$) not glued to the lower layer (3) with an internal reinforcement of Scrinyl (9 g/m$^2$) glued to the lower layer with a polyvinyl alcohol glue diluted to 5%, at a rate of 2 g/m$^2$ of glue (4) with an internal reinforcement grid of Scrinyl (9 g/m$^2$) hot melt glued to the lower layer at a rate of 7 g/m$^2$ of Belix 74101 glue (5) with a non-woven material Holnest (11 g/m$^2$) not glued (6) with a non-woven material Holnest (11 g/m²) hot melt glued to the lower layer at a rate of 7 gm/m² of Belix 74101 glue.

An after use count was made of the number of nappies whose gel had become visible through the non-woven exterior material; this number translated into percentages gave the proportion of nappies with gel visible per batch. The number of nappies whose layer had deteriorated also was counted.

The results were the following:

|     | Gel visible % | Layer deteriorated % |
| --- | --- | --- |
| (1) | >45 | 35 |
| (2) | 25 | 11 |
| (3) | 15 | 5 |
| (4) | 4 | 2 |
| (5) | 9 | 2 |
| (6) | 0 | 0 |

These results show:

Strong migration of gel in the absence of an internal reinforcement sheet, (Batch (1))

When a Scrinyl grid was used the proportion of gel visible was reduced considerably by gluing (Batches (3) and (4))—this proportion was further improved when a hot melt glue was used (Batch (4)) rather than a sprayed diluted glue (Batch (3)). This is explained by the fact that the quantity of the latter must be limited to avoid wetting the layer too much.

An excellent result is obtained when a light non-woven material, Holnest, bonded to the lower layer by means of a hot melt glue (Batch (6)). The better result obtained compared with that with the Scrinyl grid is no doubt explained by the fact that the non-woven material has a tighter mesh than the grid of equivalent grammage.

By means of a structure according to the invention (Batches (3), (4), (6)) thin nappies requiring less material and whose properties are satisfactory as regards confinement of the gel and maintenance of the layer. The results should be compared in particular with those concerning the nappies with a cross-section in the form of a snail mentioned earlier, which is more voluminous where for a layer of 350 g/m² folded over giving a pad of 700 g/m² between the non-woven material on the body side and the additive, a visible gel proportion of 20% is obtained without an intermediate non-woven material and, 8% and 4% respectively with a non-woven reinforcement material Scrinyl and non-glued Holnest.

What is claimed is:

1. An absorbent structure for hygienic disposable articles comprising a permeable sheet, an impermeable sheet, and a pad between said permeable and impermeable sheets, said pad comprising successively at least a first layer of fluffed cellulosic material that does not contain improved retention additive; an internal reinforcement layer permeable to liquids made of a non-woven material resistant to moisture and liquid, and an absorbent layer provided with improved liquid-retention additive particles, said internal reinforcement sheet being glued to said absorbent layer.

2. An absorbent structure according to claim 1 wherein said absorbent layer consists of a fiber layer, the additive particles being deposited on the surface over all or part of said layer adjacent to the internal reinforcement sheet.

3. An absorbent structure according to claim 2 wherein the reinforcement layer envelops the absorbent layer.

4. An absorbent structure according to claim 1 wherein the absorbent layer consists essentially of an improved liquid-retention additive and the reinforcement layer is glued against the impermeable sheet.

5. An absorbent structure according to claim 1 wherein the absorbent layer consists of a fiber layer incorporating improved liquid-retention additive particles.

6. An absorbent structure according to claim 1 wherein the glue is a hot melt glue.

7. An absorbent structure according to claim 1 wherein the reinforcement sheet is a grid.

8. An absorbent structure according to claim 1 wherein the reinforcement sheet is a web of bonded thermoplastic fibers.

* * * * *